US008141557B2

(12) United States Patent
Peyman (10) Patent No.: US 8,141,557 B2
(45) Date of Patent: Mar. 27, 2012

(54) METHOD OF OSCILLATORY THERMOTHERAPY OF BIOLOGICAL TISSUE

(76) Inventor: Gholam A. Peyman, Sun City, AZ (US)

(*) Notice: Subject to any disclaimer, the term of this patent is extended or adjusted under 35 U.S.C. 154(b) by 558 days.

(21) Appl. No.: 12/256,057

(22) Filed: Oct. 22, 2008

(65) Prior Publication Data

US 2010/0100162 A1 Apr. 22, 2010

(51) Int. Cl.
*A61B 19/00* (2006.01)
(52) U.S. Cl. ............... 128/898; 607/88; 607/96; 606/6
(58) Field of Classification Search ........... 607/88–91, 607/96–103; 606/4–6; 128/898
See application file for complete search history.

(56) References Cited

U.S. PATENT DOCUMENTS

| | | | | |
|---|---|---|---|---|
| 6,113,552 A * | 9/2000 | Shimazu et al. | ............... | 600/557 |
| 6,322,556 B1 * | 11/2001 | Gwon et al. | ............... | 606/6 |
| 7,402,167 B2 * | 7/2008 | Nemenov | ............... | 607/89 |
| 2006/0020309 A1 * | 1/2006 | Altshuler et al. | ............... | 607/88 |
| 2008/0177358 A1 * | 7/2008 | Gammons | ............... | 607/96 |

OTHER PUBLICATIONS

Andley, U.P., et al., "Differential Protective Activity of AlphaA- and AlphaB-Crystallin in Lens Epithelial Cells." J Biol Chem. Nov. 24, 2000; 275(47):36823-31.
Capon, A.C., "Scar Prevention by Laser-Assisted Scar Healing (LASH): A Pilot Study Using an 810-nm Diode-Laser System." Lasers Surg Med. Sep. 2008; 40(7):443-5.
Hitotsumatsu, T., et al., "Distinctive Immunohistochemical Profiles of Small Heat Shock Proteins (Heat Shock Protein 27 αB-Crystallin) in Human Brain Tumors." Cancer. Jan. 15, 1996; 77(2):352-61.
Ivanov, O., et al., "αB-Crystallin is a Novel Predictor of Resistance to Neoadjuvant Chemotherapy in Breast Cancer." Breast Cancer Res Treat. Oct. 2008;111(3):411-7. Epub Oct. 30, 2007.
Kamradt, M.C., et al., "The Small Heat Shock Protein Alpha B-Crystallin Negatively Regulates Cytochrome c-And Caspase-8-Dependent Activation of Caspase-3 by Inhibiting its Autoproteolytic Maturation." J Biol Chem. May 11, 2001;276(19):16059-63. Epub Mar. 23, 2001
Martin, J.L., et al., "Small Heat Shock Proteins and Protection Against Ischemic Injury in Cardiac Myocytes." Circulation. Dec. 16, 1997;96(12):4343-8.
Paulsen, G., et al., "Maximal Eccentric Exercise Induces a Rapid Accumulation of Small Heat Shock Proteins on Myofibrils and a Delayed HSP70 Response in Humans." Am J Physiol Regul Integr Comp Physiol. Aug. 2007;293(2): R844-53. Epub May 23, 2007.
Xi, J., et al., "A Comprehensive Analysis of the Expression of Crystallins in Mouse Retina." Mol Vis. Aug. 28, 2003; 9:410-9.
Xi, J.H., et al., "Mechanism of Small Heat Shock Protein Function in Vivo: A Knock-In Mouse Model Demonstrates That the R49C Mutation in Alpha A-Crystallin Enhances Protein Insolubility and Cell Death." J Biol Chem. Feb. 29, 2008;283(9):5801-14. Epub Dec. 5, 2007.
Yaung, J., et al., "α-Crystallin Distribution in Retinal Pigment Epithelium and Effect of Gene Knockouts on Sensitivity to Oxidative Stress." Mol Vis. Apr. 4, 2007;13: 566-77.

* cited by examiner

*Primary Examiner* — Ahmed Farah
(74) *Attorney, Agent, or Firm* — Thompson Hine LLP (57) ABSTRACT

A method for thermotherapy of a biological tissue by determining the temperature at which to heat a target site to be treated to provide a temperature to the site to effect therapy, the temperature above body temperature but below a protein denaturation temperature, as determined by a patient's experience of a sensation of pain. Thermotherapy is effected in the absence of coagulative effects by providing oscillatory energy at the predetermined temperature.

14 Claims, 5 Drawing Sheets
(5 of 5 Drawing Sheet(s) Filed in Color)

METHOD OF OSCILLATORY THERMOTHERAPY OF BIOLOGICAL TISSUE

A method to determine and control parameters for thermotherapy of a biological tissue to achieve a temperature below that at which protein denaturation occurs. Assessing the time at which a patient expresses a sensation of pain when exposed to an elevated temperature, relative to body temperature, accurately precludes exposing the patient to a temperature at which proteins denature during thermotherapy.

The method encompasses the use of any type of thermotherapy including, but not limited to, laser therapy, photodynamic therapy, and transpupillary therapy. Therapy refers to any amelioration of pathological effects, including lessening severity, lessening symptoms, etc. Complete treatment efficacy is included, but is not required.

Laser coagulation therapy has long been used to treat retinal and choroidal disease (Ophthalmic Surg. 13 (1982) 928). Laser coagulation produces its effect when ocular tissues, such as retinal pigments and/or fluids, absorb light energy (visible, infrared) and are exposed to increased temperatures to result in protein denaturation, that is, coagulation. As a result, laser coagulation is a tissue destructive method. It therefore cannot be performed over the center part of the fovea, which is the most visually sensitive part of the retina, because these tissues will be permanently damaged and visual function will be lost. Laser coagulation has been effectively used in peripheral portions of the retina and choroid to close abnormal vessels, for example, as a result of diabetes or subretinal extra-foveal neovascularization. In some cases, however, laser coagulation can lead to vision loss because of growth of the laser spot and/or scar over time, or because subretinal neovascularization causes bleeding, or incites new vessel growth.

Photodynamic therapy (PDT) uses laser light along, with a photosensitizer injected intravenously, to achieve its effect, for example, vascular occlusion. The photosensitizer, upon light activation, releases in the vessel singlet oxygen that damages the vessels and causes platelet aggregation and blood clots. PDT is more protective to the retina than laser coagulative and can be used over the fovea. However, it requires multiple treatments to close abnormal vessels, and produces a scar under the fovea and reduces vision over time (Ophthalmology 107 (2000) 29).

Transpupillary thermotherapy (TTT) has been used to treat wet age-related macular degeneration (ARMD), which exhibits abnormal subretinal vessels (Retina 25 (2005) 1046; Retina 23 (2003) 378); Retina 23 (2003) 371, and U.S. Pat. No. 6,887,261. It had been thought that laser light in the infrared wavelength applied over a prolonged period could produce a hyperthermic effect without coagulating the retina, but in practice it was not possible to use the standard treatment parameters advocated by the manufacturer to prevent destructive coagulative laser effects. Because of the variability in the amount of ocular pigmentation, the same energy would produce coagulation in a pigmented area and have no effect in non-pigmented areas. There was also no way to non-invasively measure the temperature of the retina or the choroid.

Each of laser coagulation, PDT, and TTT lack a reliable method to non-invasively measure temperature inside the tissue to be treated. Therefore, the temperature needed to safely and predictably achieve the desired therapy could not readily be determined.

The disclosed method employs a relationship between the patient's expression of a sensation of pain when exposed to an elevated temperature, relative to body temperature, and the temperature increase upon application of thermal energy to achieve a desired therapeutic effect, in the absence of a detrimental protein denaturation effect, as referred to as a coagulative effect.

The patent or application file contains at least one drawing executed in color. Copies of this patent or patent application publication with color drawing(s) will be provided by the Office upon request and payment of the necessary fee.

As shown in Table 1 below, measuring the time at which the patient expresses a sensation of pain when exposed to elevated temperatures, relative to body temperature, accurately precludes exposing the patient to a temperature at which proteins denature. Data are from a normal individual immersing a finger in water at the stated temperature and duration, and recording a relative subjective sensation of pain.

TABLE 1

| WATER TEMPERATURE | EXPOSURE TIME BEFORE WITHDRAWAL | SENSATION |
| --- | --- | --- |
| 140° F. = 60° C. | Immediate | strong pain |
| 130° F. = 54.4° C. | 7 seconds | pain |
| 120° F. = 48.9° C. | 15 seconds | pain |
| 115° F. = 46.1° C. | >7 min | warmth |
| 110° F. = 43.3° C. | >7 min | warmth |

From Table 1, the sensation of pain occurred at a temperature above about 46° C. When a biological cell is exposed to a temperature of about 43° C., it produces heat shock proteins (HSP), which are proteins that protect biological cells against adverse agents and effects (e.g., oxidative agents, agents that result in chemical and/or metabolic stress, etc.). When a biological cell is exposed to a temperature of about 60° C., its proteins denature, and protein denaturation elicits an immediate and strong pain sensation.

Various treatment methods have been explored to reduce macular edema and/or central macular thickness (CMT). Treatment with intravitreal injections of bevacizumab (IVB) alone, or in combination with invitreal injections of triamcinolone acetonide (IVT), or macular photocoagulation have not produced satisfactory results. As described in Example I below, only a transient reduction in central macular thickness was achieved in all groups, lasting up to only 6 weeks. Thus, a method for reducing macular edema and/or CMT is needed.

In one embodiment the method is used to reduce undesirable cell proliferation at various anatomical and/or physiological sites, termed a target tissue or target cells. A known by a person of ordinary skill in the art, a tissue is a organization of cells. In one embodiment, the method is used in the eye to reduce cell proliferation in the choroid, retina, and/or lens capsule. In one embodiment, the method is used to selectively trigger apoptosis in target cells, such as cells that are heat sensitive, abnormal, immature, and/or growing, while leaving normal cells unaffected. For example, when used in the eye, the method may selectively damage abnormal cells in the retina while leaving normal retinal cells and optic nerve cells undamaged.

The method may also render normal cells less sensitive to metabolic damage and oxidative stress by inducing HSP production. In one embodiment, the method thermally and optionally, chemically, treats cells at anatomical and/or physiological sites to induce apoptosis, or impede cell multiplication, without causing cellular protein denaturation.

The method creates, in the target tissue, hyperthermia; i.e., a temperature elevated over body temperature, thus a temperature greater than about 37° C., but less than about 60° C., which is the temperature at which protein denaturation occurs. In one embodiment, the method creates hyperthermia in the target tissue of greater than about 37° C., but less than about 46° C., to facilitate HSP production and/or other hyperthermic effects.

The method minimizes inhibits selective cell growth and/or proliferation.

In treating macular edema, a temperature is selected based upon the patient's specific tolerance for pain. In subsequent thermal treatments, the temperature is maintained below the selected temperature during laser therapy to inhibit cell growth and reduce edema.

In one embodiment, the method uses a patient's subjective evaluation of his/her own pain threshold as a real-time indicator of temperature of the tissue. A pain threshold temperature is determined that is above body temperature but below a temperature at which protein denaturation is initiated. By maintaining the temperature below the temperature at which the patient experiences a sensation of pain, the temperature required for a beneficial effect without protein denaturation and tissue damage is achieved.

Beneficial effects of thermotherapy include release of HSP and inhibition of cell division. For example, levels of the HSP Hsp27 and αB-crystallin in C6 rat glioma cells that had been heated at 43° for 30 min, with subsequent culture at 37° C. for 16 h, were markedly increased (Cell Stress Chaperones 4 (1999) 94; Biochem Biophys Res Commun 26 (2002) 854; J Biol Chem 275 (2000) 4565; and J Cell Physiol 166 (1996) 332). HSP such as HSP27 and α-crystallins also play an important role in the resistance to anticancer drugs); protect lens epithelial cells from apoptosis (J Biol Chem 275 (2000) 3682; Breast Cancer Res Treat 111 (2008) 411;) J Biol Chem 276 (2001) 16059); provide protection against TNFα-mediated cell death and other types of oxidative stress (EMBO J 15 (1996) 2695); participate in regulating cell proliferation (Cancer 77 (1996) 352); maintain cytoskeleton integrity (J Neurosci Res 66 (2001) 59); protect retinal pigment epithelium (RPE) from susceptibility to oxidative stress (Mol Vis. 13 (2007) 566); protect retinal neurons from environmental and/or metabolic stress damage (Mol Vis. 9 (2003) 410); play a role in pathophysiology of diabetic complications (Arch Biochem Biophys. 444 (2005) 77); defend against dysregulated proteins (J Neurosci Res 86 (2008) 1343); and protect against ischemic injury (Circulation 96 (1997) 4343). Point mutations in the αA-crystallin gene cause congenital human cataracts (J Biol Chem 283 (2008) 5801). Lack of α-crystallins accentuated retinal degeneration in chemically induced hypoxia in vivo (Exp Eye Res 86 (2008) 355).

Thermotherapy performed by laser irradiation, at non-coagulative or low-level laser light, has an anti-inflammatory effect on tissues (Lasers Surg Med 40 (2008) 500; Inflammation 31 (2008) 189; and Photomed Laser Surg 26 (2008) 19), and prevents scar formation (Lasers Surg Med 40 (2008) 443; Lasers Surg Med 28 (2001) 168; and Lasers Surg Med 40 (2008) 159).

In one embodiment, the method enhances penetration of medicaments into tissue. It is known that thermotherapy enhances penetration of medication into tissues and thereby enhances the effect of these medications (Lasers Surg Med 40 (2008) 468). Hyperthermic effects enhance efficacy of a medication's effect on tissues by increased tissue penetration and reabsorption of preexisting intra- and inter-cellular fluid which otherwise causes tissue edema. Thermotherapy increases blood circulation, which also enhances drug delivery to the tissue by expanding the capillaries and vasculature at the site of interest, thus increasing blood flow to the site.

In one embodiment, the method uses an energy emitting device to selectively heat tissues at a desired site to a temperature that kills the cells without causing protein denaturation in the cells. Any thermal source may be used. In one embodiment, light is used as a heat source. In one embodiment, ultrasound is used as a heat source. In one embodiment, heating occurs with chemical treatment to change a cell physical characteristic to thus cause cell death or impede cell multiplication. Such devices with and without chemical treatment are disclosed in U.S. Pat. No. 6,887,261.

In one embodiment, the method uses an energy emitting device and a positioning device that is adapted to position the energy emitting device relative to the cells at the site to be treated. In embodiments, the positioning device aims and/or manipulates the energy emission from the energy emitting device. For example, the positioning device may includes a slit-lamp, ophthalmoscope, microscope, fiber optic conduit, reflector, mirror, lens, camera, and other imaging systems including magnetic resonance imaging (MRI) and computed tomography (CT).

In one embodiment, the method uses a laser to effect hyperthermia in the tissue at the desired anatomical and/or physiological site. Suitable lasers as a source of energy (heat) include all visible light sources that are capable of producing thermal effect from 400 nm to 750 nm, all electromagnetic radiation sources that are capable of producing thermal effect from 750 nm to 1.7 M, and ultraviolet light sources from about 280 nm to 400 nm, using an individual wave length or a collection of wavelengths. Alternatively, a source of energy can be ultrasound, microwave, or other electromagnetic radiation that will sufficiently heat to thermally treat cells as described. In one embodiment, the power output of, for example, a laser, is adjustable to the desired level from 1 mW to 1.5 W.

The method uses an oscillating energy source. This achieves therapeutic temperature levels in the tissue, without causing protein denaturation and thermal coagulation of the tissue, resulting in tissue burning and necrosis. In contrast to the inventive method, ocular tissue treated with TTT uses a stationary laser that is focused on a single large area that treats the entire area and delivers constant energy over the entire spot.

The tissue, or portion of tissue, is exposed to the energy source that is provided in an oscillatory manner. Oscillation describes a changing level of energy being received by the target tissue. In one embodiment, the changing level in the energy received by the target tissue is defined by the maximum and minimum energies received, and/or the periodicity, e.g., the time interval between consecutive maximum energy level being received by the target tissue. In one embodiment, the output of the energy source is moved relative to the target tissue. For example, in the case of a laser, the laser beam is moved over the target area such that no point in the target area receives constant illumination.

In one embodiment, oscillation is achieved by pulsing the energy emission. In one embodiment, oscillation is achieved by a combination of moving the emission of the energy source and intermittently applying energy to the target tissue. In one embodiment, the maximum energy in the target tissue is less than or equal to the pain sensation threshold energy level. For example, during oscillatory thermotherapy, the maximum energy directed to the target tissue is less than or equal to the energy level which elicited a pain response in the particular patient.

In one embodiment, oscillation can be achieved by a hand held manipulator. In one embodiment, oscillation can be achieved by an electromechanically movable manipulator with an adjustable control system to control the extent and direction of energy emission, such as by adjusting raster form, right and left traverse, up and down traverse, size and/or shape of energy emission beam such as semicircular or circular, and/or motion. In one embodiment, oscillation can be achieved by a pulsed laser. A pulsed laser can be adjusted to cover the entire target area of tissue, or can use a shotgun approach with areas of overlapping in raster, or circular fashion, or random fashion over the target area of tissue. In one embodiment, oscillation can be achieved using a combination of motion induced mechanical and pulsing emission. In one embodiment, a timer that emits an audible and/or visual signal to indicate the time elapsed to control the degree of energy needed may be used. In one embodiment, oscillatory thermotherapy is controlled remotely, e.g., via the Internet.

In one embodiment, a system is provided with controls to adjust the spot size of energy emission, e.g. light, on the desired target area. In one embodiment, the spot size of energy emission ranges from about 0.05 mm to about 8 mm or more by using, e.g., an aperture, a lens, a mirror, etc. In one embodiment, the spot size ranges from about one third to about one half the size of the target site, e.g. lesion, to be treated. In one embodiment, the target tissue is exposed to oscillatory energy, e.g., moving or intermittent energy, for up to about 1 minute to about 7 minutes, or as needed.

One embodiment is a test mode, in which the maximum energy emission to be applied to a target tissue is pre-determined by assessing exposure to a non-target tissue (e.g., normal retina, normal choroid, etc.). In this test mode embodiment, the laser or other energy source is applied in a non-oscillatory mode for about 10 seconds up to about 30 seconds at a setting such that the patient does not experience a sensation of pain. In one embodiment using the test mode, the laser is applied in a non-oscillatory mode for about 10 seconds to about 20 seconds without the patient experiencing a sensation of pain. In one embodiment using the test mode, the spot size is from about 100 µm to about 4000 µm. In this way, the energy setting that does not result in a sensation of pain and that does not produce any coagulative necrotic tissue damage to the target tissue is determined. Thus, when the target tissue is then treated with oscillatory energy at or below the pre-determined energy level, the practitioner is assured that no protein coagulation and/or denaturation will occur in the target tissue. This is because the tissue temperature is reduced during energy oscillation, e.g., with an oscillation of about 1/sec or less up to an oscillation of about 100/sec or more. Oscillating thermal energy provides sufficient tissue cooling by, e.g., thermal conduction, reflection, or blood circulation, while still providing sufficient heat to induce beneficial effects, such as HSP production, etc.

In one embodiment, the target tissue is exposed to oscillatory energy in a pre-heat mode prior to exposure to oscillatory energy in a treatment mode. In one embodiment, the tissue is exposed to laser energy for about 0.5 minute to about 2 minutes prior to treatment with oscillatory energy. In one embodiment, when the tissue to be treated is about 200 µm thick to about 250 µm thick, pre-heat treatment occurs for about 1.5 minutes (90 seconds). In one embodiment, when the tissue is thicker than 250 µm, for each additional 100 µm in thickness, the duration of the pre-heat treatment is increased about 1.5 times. For example, a tissue that is about 450 µm thick is pre-heated for about 4.5 minutes before treatment for about 4.5 minutes. In one embodiment, the amount of time and oscillatory energy to which the tissue is equal to the amount of time and energy that was used to pre-heat the tissue. In embodiments where a biocompatible dye is employed, the dye may be injected or otherwise provide during and/or following the pre-heat treatment.

The extent of treatment, which as described above includes any of energy output, duration of exposure to energy, size of target spot, parameters of oscillation of energy exposure, etc., are varied depending on several factors. One factor accounts for the volume of fluid in the target tissue. For example, an edematous tissue may require increased treatment to achieve a desired effect relative to a non-edematous tissue; this may take the form of increased energy output, increased duration of exposure to energy, etc. One factor accounts for the presence and/or extent of pigmentation in the target tissue. Pigmentation affects the amount of energy in the form of light that is absorbed by the tissue; pigmented tissues more readily absorb light energy and thus exhibit a larger temperature increase than a less pigmented tissue for a given energy emission. For example, a pigmented tissue will require less treatment than a non-pigmented or less pigmented tissue; this may take the form of decreased energy output, decreased duration of exposure to energy, etc. All of these factors are taken into consideration when a patient expresses pain sensation with a given energy and time of exposure.

In one embodiment, one or more additional components that enhance absorbance of the thermal energy are included with the method. In one embodiment, a device to provide the additional components to the target site is used. The device can be unitary with or separate from the energy emitting device. In one embodiment, the energy emission used to heat the tissue may be the same or different than the energy source used to activate the additional component, for example, by emitting light at the same or different wavelength. In one embodiment, the additional component is a biocompatible dye, examples of which include but are not limited to indocyanine green (ICG), vorteporfin, rose bengal, liassamine green, etc. In one embodiment, the biocompatible dye is indocyanine green. The dye lowers the amount of energy needed for therapy, thus decreasing damage to the normal adjacent tissue while providing therapy to target tissue. In one embodiment, the energy emitting device can be controlled to direct energy, e.g. light, onto the target site to activate a dye present at the target site cells to alter at least one physical characteristic of the tissues/cells at the target site. In one embodiment, a systemic dye, e.g. a photosensitizer, can be used to absorb light energy and increase the temperature at the location and/or produce a limited additional photodynamic effect inside a vessel, as described in U.S. Pat. No. 6,936,043.

For example, the dye ICG may be used with oscillatory thermotherapy. The dye may be introduced, e.g. injected, before, during, or after oscillatory thermotherapy. The dye may be activated before, during, or after oscillatory thermotherapy. In one embodiment, injecting ICG or any other appropriate dye, during oscillatory thermotherapy enhances a thermal effect because the dye in the vessel at a target site absorbs the energy, which facilitates selective apoptosis of immature endothelial cells without coagulating adjacent normal tissue.

ICG is known in the art and used in ophthalmology and cardiology for angiography of the back of the eye and for cardiac function, respectively. Specifically, ICG has been used to enhance coagulation of portions of the eye. ICG absorbs at a wavelength between about 800 nm and about 810 nm, and fluoresces at a wavelength between about 820 nm and about 830 nm, as described in U.S. Pat. Nos. 2,895,955 and 6,887,261.

In one embodiment, the method is performed in the eye. When a choroidal vessel is the target site, it can be closed or altered more rapidly, and/or at lower power levels, than retinal vessels. Thus, treatment of choroidal neovascularization in ARMD is achieved while simultaneously protecting retinal vessels.

In one embodiment, before, during or after the energy emitting device is controlled to heat the cells in the manner described above, a photosensitizer is provided at a target site, e.g., retina. In one embodiment, the photosensitizer is administered locally, e.g., by injection. In one embodiment, the photosensitizer is administered systemically. Upon thermally treatment of retinal tissues by energy, e.g. light, emitted from an energy emitting device, the energy emitting device is controlled to activate the photosensitizer, e.g., by emitting light having a wavelength that activates the photosensitizer at the target site, e.g., absorbed by, or located within or adjacent to the target site. In one embodiment, OTT is performed for some treatment period, e.g. one half of the entire treatment period, followed by introduction of a dye, e.g. ICG, and OTT in the presence of dye is performed for the remaining treatment period. In one embodiment, PDT as described in U.S. Pat. No. 6,936,043 is performed in conjunction with an oscillating energy source.

In one embodiment, additional agents may be included in the method. These additional agents may be locally and/or systemically provided. Examples of such agents include, but are not limited to, anti-inflammatory agents, steroids, non-steroidal anti-inflammatory drugs (NSAIDS), anti-vascular endothelial growth factor (VEGF) agents, anti-platelet derived growth factor (PDGF) agents, anti-proliferative agents, metalloproteinase inhibitors, and/or penetration enhancing agents. NSAIDs selectively enhance HSP production and thus their administration can be controlled to achieve a desired effect using the disclosed method.

Examples of such additional agents include, but are not limited to, the following: colchicine; a steroid such as triamcinolone (Aristocort®; Kenalog®), anacortave acetate (Alcon), betamethasone (Celestone®), budesonide Cortisone, dexamethasone (Decadron-LA®; Decadron® phosphate; Maxidex® and Tobradex® (Alcon)), hydrocortisone methylprednisolone (Depo-Medrol®, Solu-Medrol®), prednisolone (prednisolone acetate, e.g., Pred Forte® (Allergan), Econopred and Econopred Plus® (Alcon), AK-Tate® (Akorn), Pred Mild® (Allergan), prednisone sodium phosphate (Inflamase Mild and Inflamase Forte® (Ciba), Metreton® (Schering), AK-Prede (Akorn)), fluorometholone (fluorometholone acetate (Flarex® (Alcon), Eflone®), fluorometholone alcohol (FML® and FML-Mild®, (Allergan), FluorOP®), rimexolone (Vexol® (Alcon)), medrysone alcohol (HMS® (Allergan)), lotoprednol etabonate (Lotemax® and Alrexe (Bausch & Lomb), and 11-desoxcortisol; an anti-prostaglandin such as indomethacin; ketorolac tromethamine; ((+)-5-benzoyl-2,3-dihydro-1H-pyrrolizine-1-carboxylic acid, a compound with 2-amino-2-(hydroxymethyl)-1,3-propanediol (1:1) (ACULAR® Allegan), OCUFEN® (flurbiprofen sodium 0.03%), meclofenamate, fluorbiprofen, and the pyrrolo-pyrrole group of non-steroidal anti-inflammatory drugs; a macrolide such as sirolimus (rapamycin), pimocrolous, tacrolimus (FK506), cyclosporine (Arrestase), everolimus 40-O-(2-hydroxymethylenrapamycin), ascomycin, erythromycin, azithromycin, clarithromycin, clindamycin, lincomycin, dirithromycin, josamycin, spiramycin, diacetyl-midecamycin, tylosin, roxithromycin, ABT-773, telithromycin, leucomycins, lincosamide, biolimus, ABT-578 (methylrapamycin), and derivatives of rapamycin such as temsirolimus (CCI-779, Wyeth) and AP23573 (Ariad); a non-steroidal anti-inflammatory drug such as derivatives of acetic acid (e.g. diclofenac and ketorolac (Toradol®, Voltaren®, Voltaren-XR®, Cataflam®)); salicylate (e.g., aspirin, Ecotrin®), proprionic acid (e.g., ibuprofen (Advil®, Motrin®, Medipren®, Nuprin®)); acetaminophen (Tylenol®), aniline (e.g., aminophenolacetaminophen, pyrazole (e.g., phenylbutazone), N-arylanthranilic acid (fenamates) (e.g., meclofenamate), indole (e.g., indomethacin (Indocin®, Indocin-SR®)), oxicam (e.g., piroxicam (Feldene®)), pyrrol-pyrrole group (e.g., Acular®), antiplatelet medications, choline magnesium salicylate (Trilisate®)), cox-2 inhibitors (meloxicam (Mobic®)), diflunisal (Dolobid®), etodolac (Lodine®)), fenoprofen (Nalfon®), flurbiprofen (Ansaid®), ketoprofen (Orudis®, Oruvail®), meclofenamate (Meclomen®), nabumetone (Relafen®), naproxen (Naprosyn®, Naprelan®, Anaprox®, Aleve®), oxaprozin (Daypro®), phenylbutazone (Butazolidine®), salsalate (Disalcid®, Salflex®), tolmetin (Tolectin®), valdecoxib (Bextra®), sulindac (Clinoril®), and flurbiprofin sodium (Ocufen®), an MMP inhibitor such as doxycycline, TIMP-1, TIMP-2, TIMP-3, TIMP-4; MMP1, MMP2, MMP3, Batimastat (BB-94), TAPI-2,10-phenanthroline, and marimastat. The composition may contain anti-VEGF agents such as ranibizumab (Lucentis®, Genentech) and/or pegaptanib (Macugen®). The composition may contain anti-PDGF agents such as imatinib mesylate (Gleevec®) and/or anti-leukotriene(s) such as genleuton, montelukast, cinalukast, zafirlukast, pranlukast, zileuton, BAYX1005, LY171883, and MK-571 to account for the involvement of factors besides VEGF in neovascularization. The composition may additionally contain other agents including, but not limited to, transforming growth factor β (TGFβ), interleukin-10 (IL-10), aspirin, a vitamin, and/or an antineoplastic agent.

The concentration of anti-inflammatory agent used in a particular embodiment may depend upon the particular class of agent (e.g., steroid, anti-prostaglandin, etc.), and/or particular agent (e.g., a lipophilic compound versus a water-soluble compound), and/or its formulation (e.g., extended release, delayed release, etc.), and/or its route of administration (e.g., intraocular injection versus systemic administration), and/or patient specific variables (e.g., fast or slow metabolizer, age, gender) etc. as will be appreciated by one skilled in the art.

Examples of NSAIDs include, but are not limited to, derivatives of acetic acid (e.g. diclofenac and ketorolac (Toradol®, Voltaren®, Voltaren-XR®, Cataflam®)); salicylate (e.g., aspirin, Ecotrin®); proprionic acid (e.g., ibuprofen (Advil®, Motrin®, Medipren®, Nuprin®)); acetaminophen (Tylenol®); aniline (e.g., aminophenolacetaminophen; pyrazole (e.g., phenylbutazone); N-arylanthranilic acid (fenamates) (e.g., meclofenamate); indole (e.g., indomethacin (Indocin®, Indocin-SR®)); oxicam (e.g., piroxicam (Feldene®)); pyrrol-pyrrole group (e.g., Acular®); antiplatelet medications; choline magnesium salicylate (Trilisate®), cox-2 inhibitors (meloxicam (Mobic®); diflunisal (Dolobid®), etodolac (Lodine®); fenoprofen (Nalfon®), flurbiprofen (Ansaid®);

ketoprofen (Orudis®, Oruvail®); meclofenamate (Meclomen®); nabumetone (Relafen®); naproxen (Naprosyn®, Naprelan®, Anaprox®, Aleve®); oxaprozin (Daypro®); phenylbutazone (Butazolidine®); salsalate (Disalcid®, Salflex®); tolmetin (Tolectin®); valdecoxib (Bextra®); sulindac (Clinoril®); flurbiprofin sodium (Ocufen®).

Matrix metalloproteinases (MMPs) are zinc-dependent proteinase enzymes that are associated with the tumorigenic process, and/or collagenases. These enzymes are used in the angiogenic process as well as in tumor metastasis and extracellular matrix (ECM) remodeling. Inhibitors of matrix metalloproteinases may include doxycycline and naturally occurring proteins such as the family of tissue inhibitors of metalloproteinases (TIMPs), such as TIMP-1 and TIMP-2 that are involved with the inhibition of angiogenesis and are capable of inhibiting tumor growth, invasion, and metastasis which has been related to MMP inhibitory activity; TIMP-3 which is found only in the extracellular matrix; and TIMP-4 which may function in a tissue-specific fashion in extracellular matrix hemostasis; collagenase (MMP1) which degrades fibrillar interstitial collagens, gelatinase (MMP2) which mainly degrades type IV collagen, and stromelysin (MMP3) which has a wider range of action; and synthetic metalloproteinase inhibitors such as Batimastat (BB-94) and marimastat (BB-2516) which potently and specifically inhibit metalloproteinase production. These inhibitors degrade the extracellular matrix, promoting tumor invasion and metastasis, but also regulate host defense mechanisms and normal cell function. Selective inhibition is expected to inhibit reactions leading to vascularization.

Various diseases and/or conditions can be treated with the method, including ARMD (wet or dry), diabetic macular edema, abnormal subretinal vessels caused by, e.g., previous histoplasmosis infection, etc., dermatological conditions such as loose/wrinkled skin, and scaring, and varicose veins, abnormal blood vessel formation in the skin, prevention of scarring, and cosmetic surgery. Tissues/cells at various anatomic/physiologic sites in the body can be treated using the disclosed method. Sites include, but are not limited to, eye, vessels, skin, mucous membranes, nose, ear, intestine, vagina, uterus, bladder, urethra, prostate, rectum, sinuses, brain, breast, heart, etc. The manner in which the method is used to treat these sites is similar to that described herein and is known by a person of ordinary skill in the art. As one example, body cavities such as the bladder or prostate may be treated using an internal probe to provide a thermal effect at the target site; in embodiments where dye is added, it may be injected systemically or locally. As another example, skin may be treated using an external device to provide a thermal effect at the target site; in embodiments where dye is added, it may be applied locally at the site.

ARMD is an angiogenesis-mediated ocular disorder in humans and is the leading cause of visual loss in individuals over age 55. There are two major clinical types of AMD: non-exudative or dry type, and exudative or wet type. A pathological complication of ARMD is choroidal angiogenesis or choroidal neovascularization (CNV). CNV is responsible for the sudden and disabling loss of central vision. In one embodiment, the method closes or treats choroidal vessels. The non-protein coagulation temperature achieved using the method decreases the risk of damage to the retinal vessels and therefore, treatment of choroidal neovascularization in ARMD is possible, while simultaneously protecting retinal vessels.

Macular edema may cause visual loss and legal blindness in patients with diabetic retinopathy. Macular edema is the swelling of the retina due to fluid leaking from blood vessels within the macula. Diabetic macular edema is classified into focal and diffuse types. Focal macular edema is caused by foci of vascular abnormalities, primarily microaneurysms, that tend to leak fluid. Diffuse macular edema is caused by dilated capillaries in the retina. The disclosed method reduces fluid leakage and/or promotes fluid reuptake.

Histoplasmosis is contracted by inhaling dust that carries the fungal spores. The fungus can affect the eye by causing small areas of inflammation, retinal scarring, and development of abnormal blood vessels. The disclosed method reduces and/or inhibits growth of these abnormal vessels.

Dermatological conditions may be treated by the method. For example, cosmetic dermatological conditions such as wrinkles, loose skin, varicose veins, scars, etc. may be treated by the method. Thermotherapeutic effects may produce skin tightening, collagen production, closure of abnormal and/or leaky vessels, etc.

Varicose veins result from dilation and tortuosity of the superficial veins of the lower limbs. The result is discoloration, pain, swelling, and possibly ulceration of these veins. Varicose veins often involve incompetence of one or more venous valves, which allow reflux of blood within the superficial system. This can also worsen deep venous reflux and perforator reflux. Current treatments of vein insufficiency include surgical procedures such as vein stripping, ligation, and vein-segment transplant. In one embodiment, the method's thermotherapeutic effect shrinks venous tissue and reduces vein diameter. Without being held to a single theory, this results in structural transfiguration of the collagen fibrils in the vein, leading to shortened and thickened collagen fibrils in response to heat from thermal treatment.

The method will be further appreciated with respect to the following non-limiting examples.

EXAMPLE 1

Eye of individuals were treated using the disclosed method. In this trial, 129 individuals, involving 150 eyes, were evaluated for 36 weeks; a long term study.

The individuals were diagnosed with clinically significant diabetic macular edema based on Early Treatment Diabetic Retinopathy Study criteria. Exclusions were previous panretinal or focal laser photocoagulation, prior intraocular surgery or injection, history of glaucoma or ocular hypertension, visual acuity (VA) of 20/40 or better or worse than 20/300, presence of iris neovascularization, high risk proliferative diabetic retinopathy, significant lens opacity, monocularity, pregnancy, and serum creatinine ≧3 mg/dl.

Complete ophthalmic examinations were performed as a baseline assessment. Examinations included best-corrected VA, slit-lamp biomicroscopy, tonometry, and funduscopy. Para-clinic evaluations of fundus photography, fluorescein angiography, and optical coherence tomography were performed. Best-corrected VA by the Snellen chart was recorded in logarithm of minimum angle of resolution (logMAR) scale. Lens opacity was graded from 0 to 4+ clinically. Optical coherence tomography mapping was performed using commercially available equipment (Zeiss, Dublin, Calif.). Retinal thickness was measured in a circle (3.5 mm diameter) centered on the fixation point. Mean thickness on a 1 mm circle centered on the fovea, and central macular thickness (CMT) was recorded and considered for statistical analysis.

Eligible eyes were allocated to one of three study groups: eyes receiving intravitreal bevacizumab injection alone (IVB group); eyes receiving intravitreal bevacizumab injection plus intravitreal triamcinolone (IVB/IVT group); and eyes undergoing macular photocoagulation (MPC group). In bilateral cases, each eye was enrolled in the study individually; hence, both eyes of one patient could be allocated in one group.

Indications for retreatment were persistent clinically significant macular edema if visual acuity was not better than 20/40. Retreatments were performed at 12-week intervals as required.

Injections were performed under restricted sterile condition, use of anesthetic eye drops, and insertion of a lid speculum. For the IVB group, 0.05 mL (1.25 mg) bevacizumab (Avastine; Genentech Inc., South San Francisco, Calif. (made for F. Hoffmann-La Roche Ltd., Basel Switzerland) was injected intravitrally with a 27-gauge needle through the supratemporal quadrant. For the IVB/IVT group, in addition to the intravitreal bevacizumab injection, 0.05 mL (2 mg) of triamcinolone was intravitrally injected with another 27-gauge needle through the inferotemporal quadrant. In bilateral cases, the injection in the second eye was performed after two days. In the MPC group, standard focal and/or modified grid laser was performed.

Individuals who received injections were examined at 1 and 7 days after injections for anterior chamber reaction and to measure intraocular pressure. Complete ocular examination and optical coherence tomography were performed again at 6, 12, 24, and 36 weeks. Fluorescein angiography was repeated as needed. Blood pressure was measured initially and at each visit.

The primary outcome measure was a change in best-corrected visual acuity (iogMAR) at weeks 6, 12, 24, and 36. Secondary outcomes were CMT changes by optical coherence tomography and potential injection-related complications.

A sample size of 50 eyes for each group was required to have a 90% power for detection of 0.2 logMAR difference (equal to 2 Snellen lines) in the mean VA among the groups as significant (at the two-sided 5% level), with an assumed standard deviation of 0.33.

Randomization was performed using a random block permutation method according to a computer generated randomization list. The block length varied randomly. Random allocation sequence was performed by a biostatistician. The study investigators did not know the detail of series.

For masking, a sham laser procedure (20 seconds) was performed in the IVB and IVB/IVT groups by aiming the laser beam on the macula. In the MPC group, a sham injection was done using a needleless syringe pressed against the conjunctiva. To maintain masking, individuals were prevented from seeing the syringes. All procedures were performed by staff other than the study investigators to preserve investigator masking.

Best-corrected VA measurement and OCT were performed by certified examiners masked both to the randomization and to the results of previous measurements.

Statistical analysis was performed by SPSS software (version 15 SPSS Inc., Chicago Ill.). For descriptive purposes, qualitative data were reported by percentage, and quantitative data were reported by mean±SD. To compare baseline data, the Chi-square test or Fisher's exact test were used to evaluate qualitative data; analysis of variance (ANOVA) was used to evaluate quantitative data.

The following proportions were used to describe the ratio of VA and CMT improvement in each group at weeks 6, 12, 24, and 36: ((visual acuity at weeks 6, 12, 24, and 36)−(baseline visual acuity))/((baseline visual acuity)+(CMT at weeks 6, 12, 24, and 36)−baseline CMT))/(baseline CMT).

For comparing VA and CMT with baseline values within each group, a paired sample t-test was used. The marginal regression model, based on Generalized Estimating Equation (GEE) methods, was used to compare VA and CMT in the treatment groups adjusted for the baseline values, as well as to eliminate any possible correlation effects between the eyes of patients in bilateral enrolled cases.

P values less than 0.029 were considered statistically significant to control the study-wise type 1 error (primarily type 1 error was set at 0.05), based on an a spending function method (Pocock Clinical trials: a practical approach. Great Britain: John Wiley & Sons; 1990:148) for an interim analysis.

The results were as follows: 150 eyes of 129 patients were enrolled and followed from September 2005 to May 2007. Mean age of patients±SD was 61.2±6.1 years. Seventy nine patients (52.7%) were male. One hundred forty one (94%) eyes had nonproliferative diabetic retinopathy (NPDR) and 9 eyes (6%) had early proliferative diabetic retinopathy.

Eyes were randomly assigned to one of the treatment groups: (1) 50 eyes in the IVB group; (2) 50 eyes in the IVB/IVT group; and (3) 50 eyes in the MPC group. Retreatment was required for 27 eyes up to 36 weeks; 14 eyes in the IVB group, 10 eyes in the IVB/IVT group, and 3 eyes in the MPC group. Third repeated treatment was required in 3 eyes in the IVB group, 3 in the IVB/IVT group, and 1 in the MPC group.

Means and proportions of improvement of the corrected VA and CMT in each group at every visit were obtained (data not shown). Comparisons were performed after adjustment of the parameters according to their baseline quantities in order to compensate for the influence of dissimilar baseline VA and CMT on the results.

Comparing to the baseline, VA improvement was significant in the IVB groups at all follow up visits up to 36 weeks (P<0.001). In the IVB/IVT group, VA improved significantly only at weeks 6 and 12 (P=0.002 and 0.019, respectively). In the MPC group, however, VA changes in relation to the baseline did not change significantly.

In the marginal regression model, the GEE analysis demonstrated that the differences in VA changes among the groups were statistically significant only at 6 and 24 weeks (P<0.001 and P=0.012, respectively). Pairwise comparison between groups showed that the VA improvement at 6 weeks in both IVB and IVB/IVT groups was better than the MPC group (P<0.001); however, there was no significant difference between the IVB and IVB/IVT groups (P=0.199). At 24 weeks, pairwise comparison showed that the difference of VA changes between the IVB and MPC groups was significant in favor of the IVB group (P=0.003). This difference between the IVB/IVT and MPC groups was borderline (P=0.033). However, no significant difference between the IVB and IVB/IVT groups was observed (P=0.373). At 12 and 36 weeks, VA improvement was greater in the IVB group than the other groups, although the results were not significant.

To evaluate the effects of different applied treatments on Snellen VA, the percentages of eyes with more than 2 lines VA improvement were compared. Eyes with stable VA (within 2 lines changes), and eyes with more than 2 lines VA declined among the groups. Overall, the percentage of eyes with stable VA was relatively similar among the groups at all follow-ups. The percentage of cases that gained more than 2 Snellen lines was more in the IVB and IVB/IVT groups than in the MPC group. The percentage of eyes that lost more than 2 Snellen lines was higher in the MPC group than the other groups. These differences were statistically significant among the groups at 6, 12, and 24 weeks.

CMT decreased significantly in all groups, compared to baseline, only at 6 weeks. The CMT reduction was greater in the IVB group in relation to the other two treatment groups, although the differences were not significant at any follow up time.

In the marginal regression model, generalized estimating equation analysis showed no statistically significant difference in CMT changes among the three groups at any follow up time.

VA and CMT changes of these patients were compared with patients having complete data, in order to eliminate any possible bias regarding cases with missing data at any of the follow up visits. There was no significant difference.

Transient anterior chamber reaction (trace to 1+cell) was observed in 10 (20%) and 9 (18%) eyes in the IVB and IVB/IVT groups, respectively. This side effect resolved spontaneously after one week in all groups. Ocular hypertension ($\geq$23 mmHg) was detected in 8 eyes (16%) of the IVB/IVT group; it was controlled in all eyes by medical therapy, except in one eye that progressed to neovascular glaucoma. Severe lens opacity developed in 5 eyes; 4 in the IVB/IVT group and 1 in the MPC group. Initially, retinal neovascularization was observed in 4, 2, and 3 eyes in the IVB, IVB/IVT, and MPC groups, respectively. All but one of these neovascularizations were resolved; the one neovascularization was in the MPC group. Eight eyes developed early proliferative diabetic retinopathy during the study period (1 in the IVB group; 4 in the IVB/IVT group; 3 in the MPC group). These eyes remained stable during the follow up period. Ten eyes progressed to high-risk proliferative diabetic retinopathy (4 in the IVB group; 3 in the IVB/IVT group; 3 in the MPC group). These eyes were treated accordingly and excluded from the study.

No significant increases in blood pressure, thromboembolic events, and ocular complications such as vitreous hemorrhage, endophthalmitis, and retinal detachment were detected during the study. Four patients (5 eyes) passed away during the course of the trial; 2 in the IVB/IVT group; 2 in the MPC group.

A statistical adjustment was performed to lessen the effect of inadvertent substantial imbalance in baseline VA and CMT in the groups. Statistical methods could not always overcome the problem of unequal distribution of the factors among groups. No subgroup analysis such as mild versus moderate visual loss, or focal versus diffuse macular edema, was performed according to the initial characteristics of DME.

This three-arm randomized clinical trial demonstrated superiority of intravitreal injection of bevacizumab, either alone or in combination with triamcinolone acetonide, over macular laser photocoagulation in VA improvement in primary treatment of diabetic macular edema (DME). This improvement persisted longer in the IVB group (up to 36 weeks) compared to the IVB/IVT group (up to 12 weeks). In the MPC group, no VA improvement was observed at any follow-up visit. Concerning CMT reduction, there was no meaningful superiority of the IVB and IVB/IVT groups over the MPC group. Significant CMT reduction relative to baseline measurement was observed in all groups only at 6 weeks. The primary treatment of DME, triamcinolone acetonide, not only did not have any additive effect over bevacizumab, but also resulted in less favorable visual outcome in the combined treatment group.

Considering the key role of VEGF in the pathophysiology of diabetic retinopathy, VEGF blockade is an attractive therapeutic approach. Bevacizumab is a pan-VEGF blocking agent and may impair normal physiologic VEGF-mediated functions. While one might consider this as a disadvantage, its popularity, availability, and reasonable cost caused us to include it in this clinical trial.

The beneficial effect of IVB on patients with DME has been demonstrated in recent published studies, including the preliminary results of the present clinical trial. In a phase-II study, Diabetic Retinopathy Clinical Research Network (DRCRN) disclosed a median 1-line improvement at 3 weeks that was sustained through 12 weeks by two injections of either 1.25 mg or 2.5 mg IVB. The instant study demonstrated an almost 0.3 logMAR improvement in mean VA (about 3 Snellen lines), persisting for 36 weeks. The majority (72%) of cases in the instant study required only one IVB injection during the study period. Similar to our study, the DRCRN study also demonstrated inferiority of MPC compared to IVB. The DRCRN study also clarified that CMT reduction following IVB at 3 weeks appeared to plateau or decrease in most eyes between 3- and 6-week visits. This result was comparable to our results showing a diminishing effect on CMT after 6 weeks. In the DRCRN study, it was suggested that 6 weeks might be too long for an optimal second-injection interval. However, the instant study demonstrated that the therapeutic effect of a single IVB injection may persist for up to 36 weeks for VA improvement. This improvement, without a significant decrease in CMT, may be explained by increased macular perfusion rather than leakage reduction and/or fluid resorption. It has been shown that VA changes are not always parallel to CMT changes in DME.

The effective period for IVB in treating DME was reported to be 6 weeks and 12 weeks. The Pan-American Collaborative Retina Study Group reported that 20.5% of their cases required a second injection, and 7.7% of their cases required a third injection within 6 months. In the instant study, similarly, 22% and 6% of eyes required a second and third injection, respectively. These repeated injections of VEGF inhibitors may cause retinal atrophy by blocking neuroprotective cytokines. Therefore, routine prescheduled repeated injections may not be appropriate in the primary treatment of patients with DME. The decision for re-treatment should be individualized in each patient.

A recent pilot study reported the short-term beneficial effect of intravitreal ranibizumab therapy for improving VA and reducing CMT in patients with DME. Comparison among efficacy endpoints of pegaptanib, ranibizumab, and bevacizumab in DME was limited by differences in study size, study design, inclusion/exclusion criteria, drug dosage, and drug administration schedule.

Few prospective, randomized studies have evaluated the effect of intravitreal injection of triamcinolone on DME. From their 2-year study results, Gillies et al. (Ophthalmology 113 (2006) 1533) concluded that repeated IVT injections improved vision and reduced CMT in eyes with refractory DME. To enhance therapeutic effects, the instant study combined injection of IVB with IVT. No additive effects of IVT in terms of VA improvement and CMT reduction were observed. VA improvement in the IVB/IVT group lasted less than that of the IVB group (12 weeks versus 36 weeks). Without being bound by a single theory, lens opacity progression, ocular hypertension, and adverse effects of triamcinolone preservatives might be the causes for this observation. Addition of triamcinolone did not result in increased reduction in CMT in the instant study. In a recent published comparative case series on 28 eyes of 14 patients (Shimura et al, Am J Ophthalmol 145 (2008) 854), IVT (4 mg) was better than IVB in reducing CMT and improving VA. Considering the results of this study and the instant study, one may conclude that injection of either IVB or IVT alone has a better outcome than combined treatment. In Shimura's study, 16 out of 28 eyes had undergone pan-retinal photocoagulation, and 18 out of 24 eyes had a history of cataract surgery before intervention.

Both of these factors would increase the inflammatory response and might explain the greater reported effect of triamcinolone; both of these factors were among exclusion criteria in the instant study.

In the instant study, 2 mg triamcinolone (instead of the usual dosage of 4 mg), was injected first to diminish the side effects of the drug and then to avoid having a total volume of intravitreal injection >0.1 ml, which might necessitate anterior chamber paracentesis. The optimal dosage of intravitreal triamcinolone is debatable; most researchers recommend 4 mg triamcinolone for intravitreal injection, but recently Audren et al. (Am J Ophthalmol 142 (2006) 794) compared efficacy and safety of intravitreal injection of 2 mg, versus 4 mg, triamcinolone for treatment of DME, and noticed no dose differences. It has been shown that even with lower volumes of injected triamcinolone, corticosteroid receptors inside the eye become saturated.

An early treatment diabetic retinopathy study (ETDRS) trial showed that focal MPC decreased the rate of moderate visual loss in eyes with clinically significant macular edema. Lee and Olk (Ophthalmology 98 (1991)1594) demonstrated that 24.6% of eyes with diffuse DME lost three Snellen lines or more with modified grid MPC. With this treatment, only 14.5% of cases experienced vision improvement. In the instant study, mean VA did not change significantly up to 36 weeks after macular photocoagulation. VA improvement >2 Snellen lines at 36 weeks was observed in 37.0%, 25.0%, and 14.8% of the IVB, IVB/IVT, and MPC groups, respectively. Thus, considering the potential side effects of MPC such as transient increased macular edema, paracentral scotoma, subretinal fibrosis, and inadvertent foveolar burns, intravitreal bevacizumab may be preferred for primary treatment of DME compared to MPC. Although the combination of IVB and MPC may have an additive effect, this has not been proven in the short term by DRCRN. DRCRN recently demonstrated that MPC was more effective and incurred fewer side effects than IVT over a two year period for most patients with DME, although in the short term, VA was better in the IVT group. Therefore, with longer follow up, more beneficial effects of MPC may have emerged in the instant study.

Regression of retinal neovascularization was observed in 6% of eyes in both intravitrally-injected groups, and 4% of the eyes in the MPC group, in the instant study. Progression to early proliferative diabetic retinopathy was observed in 5% and 6%, and to high-risk proliferative diabetic retinopathy in 7% and 6%, respectively, in the intravitrally-injected groups and the MPC group. Retinal neovascularization regression in eyes with proliferative diabetic retinopathy in association with intravitreal bevacizumab treatment has been reported. No significant differences in neovascularization regression and progression rates observed among the groups in the instant study may be due to the low number of cases showing such events.

No hypertension, thromboembolic events, and major intravitreal injection-related complications were encountered in the instant study. Ocular hypertension ($\geq$23 mmHg) was observed in 8 eyes (16%) of the IVB/IVT group, and was controlled by anti-glaucoma medication except in one eye that progressed to neovascular glaucoma. Mild anterior chamber reaction occurred one day after injection in 20% and 18% of eyes, respectively, in the IVB and IVB/IVT groups; it spontaneously resolved within one week.

For patients presenting with DME for the first time, MPC is currently the standard treatment, but may not be ideal. The instant study compared long-term effect of bevacizumab, alone and with triamcinolone, versus laser macular photocoagulation in treatment of DME. Compared with MPC, intravitreal injection of bevacizumab effectively increased VA or up to 36 weeks, although its effect on decreasing retinal edema was transient. In 72% of eyes, this long-term beneficial effect persisted up to 36 weeks even with a single bevacizumab injection. No additive effect of triamcinolone was observed Based on these results, intravitreal injection of bevacizumab alone may be an alternative or even first line treatment in such cases.

EXAMPLE 2

A diode laser producing 870-810 nm radiation was used in the oscillatory mode as an energy source. A slit lamp was used for illuminating the fundus and delivering laser light. Topical anesthesia was used, instead of subconjunctival, peribulbar, or retrobulbar anesthesia, so the patient was able to communicate pain sensation experienced during the initial test application.

A test spot was used initially to determine pain level. The test spot was applied using stationary light to a peripheral area of the retina; the energy was not sufficient to produce coagulation. Light application was stopped if the patient experienced pain. The time of light application was usually between 10 seconds to 30 seconds. If pain occurred within 1 second to 10 seconds of application, the light energy was reduced by 50 mW increments to achieve the desired level. This energy level, or a slightly lower level, e.g. 50 mW lower level, was then used in an oscillatory mode over the fovea. A mechanical hand controlled oscillation mechanism was used with about 1 oscillation/sec to about 5 oscillation/sec. ICG at a dose of 25 mg/2 ml was intravenously injected after initiating OTT.

Each of the figures were photographs obtained using optical coherence tomography (OCT) of the macula. Preoperative photographs show a swollen retina. Post operative photographs show decreased edema and fluid loss in the retina (macula).

Figure 1:
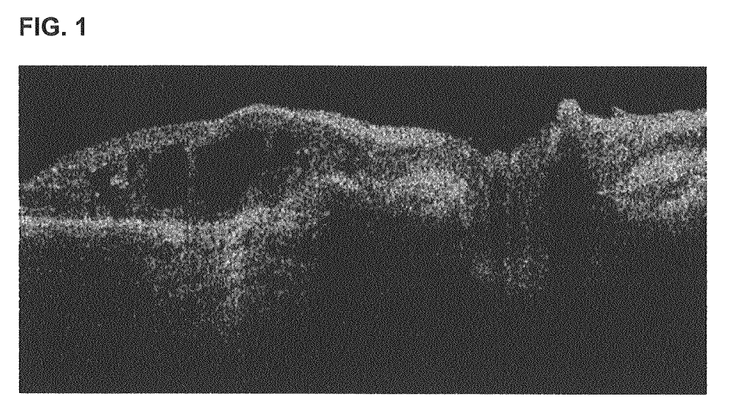
FIG. 1 shows pre-operative optical coherence tomography (OCT) of patient 1.
Figure 2:
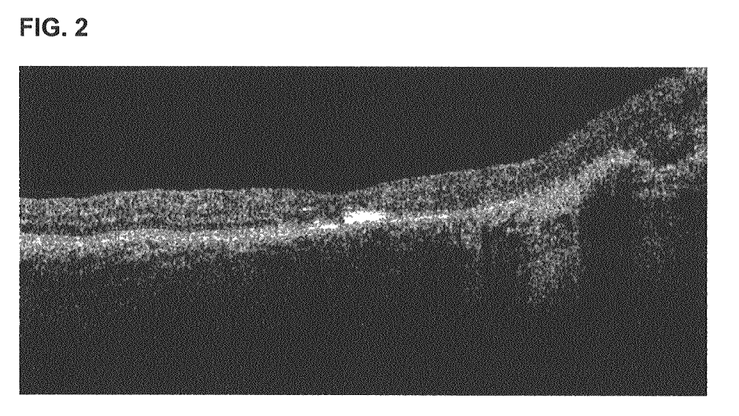
FIG. 2 shows post-operative OCT of patient 1.

FIG. 1 is from patient 1 (DG), a 48 year old male with choroidal neovascularization from histoplasmosis who had received a number of previous treatments including PDT×2, multiple TTT, multiple intravitreal injections of steroids and bevacizumab with no response. He then was treated with OTT twice with concurrent intravitreal dexamethasone on the same day. These treatments resulted in regression of the choroidal neovascular membrane regressed (FIG. 2). Since the last visit, he has maintained 20/30 vision.

Figure 3:
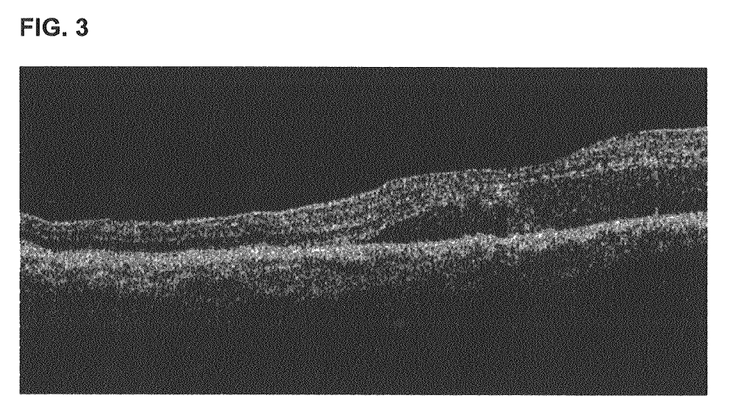
FIG. 3 shows pre-operative OCT of patient 2.
Figure 4:
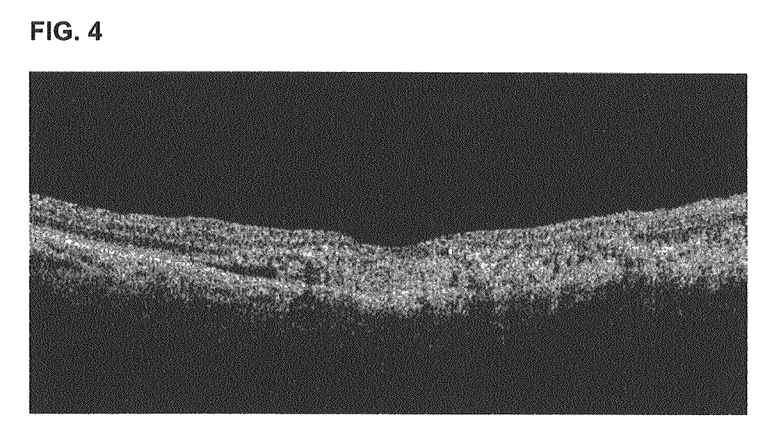
FIG. 4 shows post-operative OCT of patient 2.

FIG. 3 is from patient 2 (CR), a 69 year old female with a peripapillary choroidal neovascular membrane. Patient 2 failed previous treatments and thus was treated with oscillating TTT. Treatment parameters were 1.2 mm spot size, 200 mW power, and 90 second duration with concurrent intravitreal dexamethasone administered on the same day. These treatments resulted in OCT showing significant reduction in edema and exudates (FIG. 4).

Figure 5:
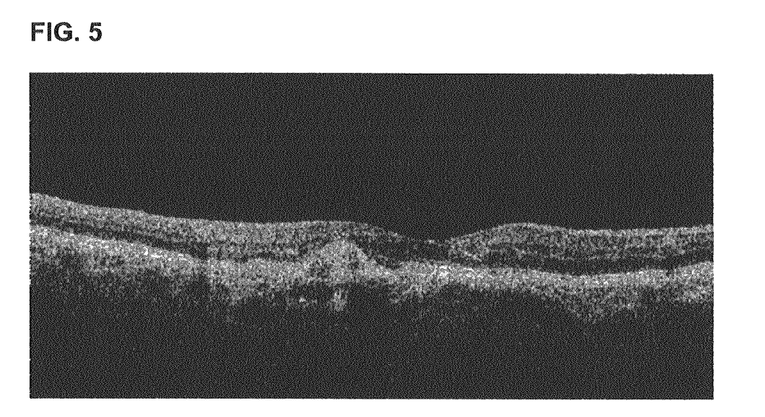
FIG. 5 shows pre-operative OCT of patient 3.
Figure 6:
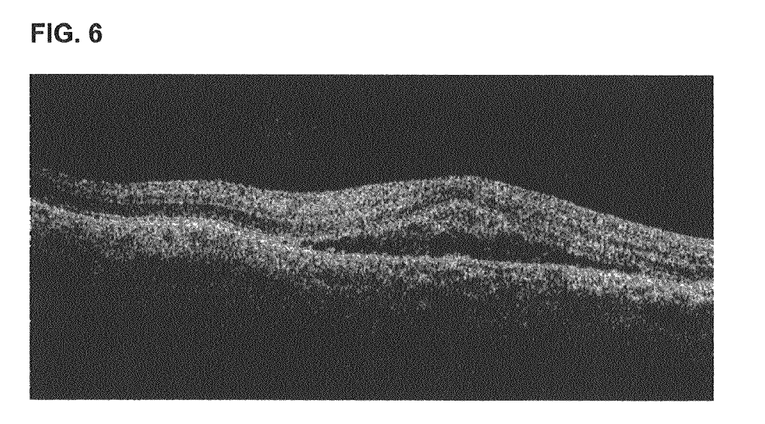
FIG. 6 shows post-operative OCT of patient 3.
Figure 7:
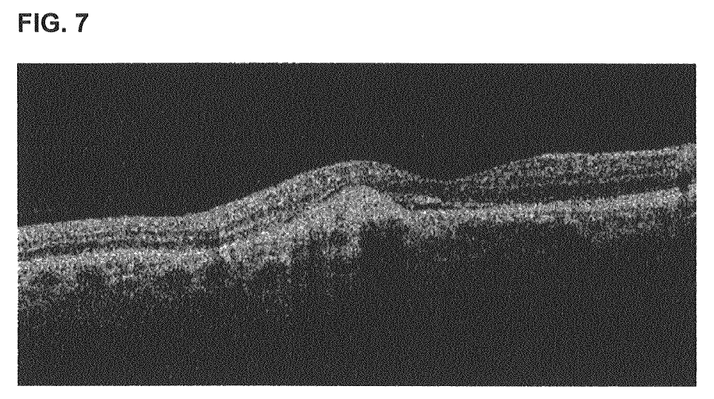
FIG. 7 shows post-operative OCT of patient 3.

FIG. 5 is from patient 3 (KJ), a 52 year old female with choroidal neovascularization from histoplasmosis who had previously been treated with laser photocoagulation, PDT and anti-VEGF agents. Patient 3 developed a stroke after one of the anti-VEGF treatments. The choroidal neovascularization recurred with vision of 20/50 and metamorphopsia. Patient 3 received one oscillating TTT treatment. Treatment parameters were 0.5 mm spot size, 200 mW power, and 60 second duration with concurrent intravitreal dexamethasone administered on the same day. About one week later, patient 3 returned with decreased vision of 20/200 (FIG. 6). OCT showed increased macular edema; edema and decreased vision resolved in one week 20/30 visions (FIG. 7). Metamorphopsia resolved with vision stabilization, but about one month later patient 3 developed a recurrence and was recently treated with intravitreal steroids and methotrexate.

Figure 8:
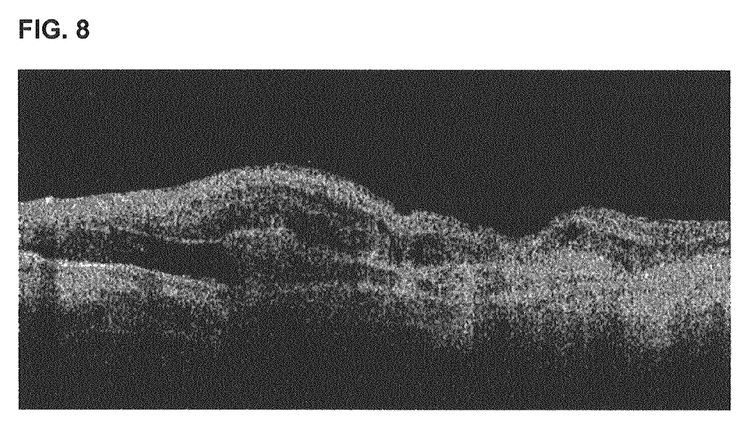
FIG. 8 shows pre-operative OCT of patient 4.
Figure 9:
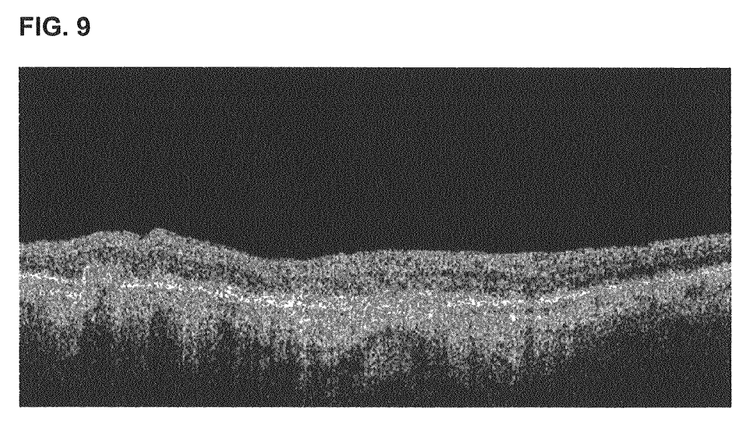
FIG. 9 shows post-operative OCT of patient 4.

FIG. 8 is from patient 4 (AH), a 90 year old male with advanced bilateral exudative macular degeneration. Patient 4 failed previous treatments including intravitreal bevacizumab. Patient 4 received one OTT treatment in the left eye. Treatment parameters were 2.0 mm spot size, 400 mW power, and 60 seconds duration with concurrent intravitreal bevacizumab administered on the same day. Patient 4 had anatomic improvement, with resolved fluid and hemorrhage (FIG. 9). Patient 9's disease was very advanced with central scarring, so there was no improvement in vision.

Figure 10:
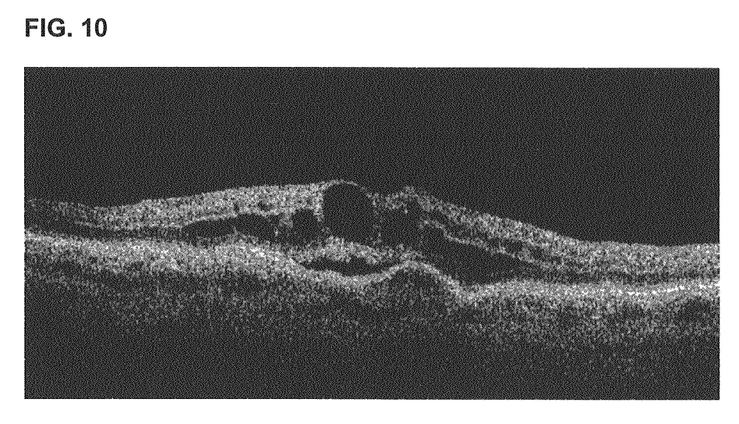
FIG. 10 shows pre-operative OCT of patient 5, right eye.
Figure 11:
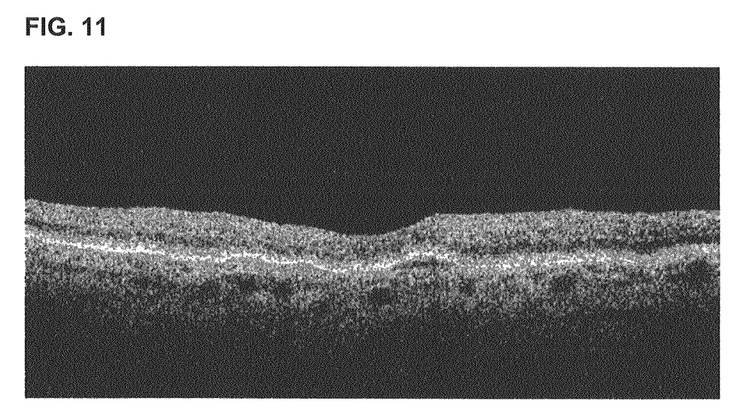
FIG. 11 shows post-operative OCT of patient 5, right eye.

FIG. 10 is from patient 5 (AF), an 80 year old diabetic female referred for significant bilateral macular edema of both eyes. Visual acuity in the right eye varied between 20/80 and 20/300. Baseline OCT of the right eye showed severe intra- and sub-retinal fluid. The central macular thickness was 396 OD, which was likely due to DME. Patient 5 received one oscillating TTT treatment to the right eye, with intravenous ICG at a follow-up appointment on day 10 after TTT treatment. At the follow-up appointment, the edema had nearly complete resolution, and the OCT showed a normal thickness of 179 μm (FIG. 11), and VA was 20/80.

Figure 12:
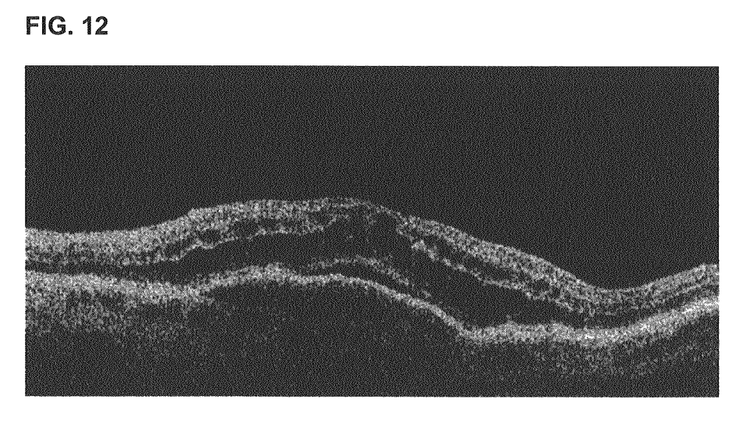
FIG. 12 shows pre-operative OCT of patient 5, left eye.
Figure 13:
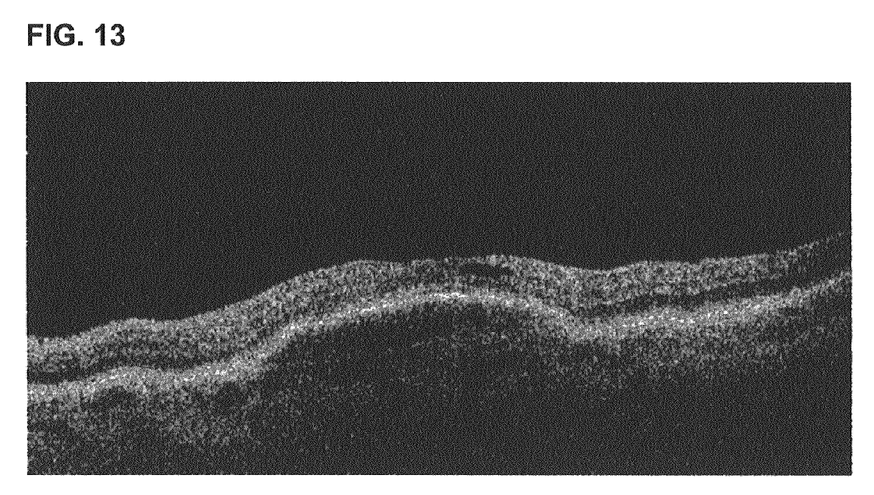
FIG. 13 shows post-operative OCT of patient 5, left eye.

FIG. 12 is also from patient 5 (AF). Baseline OCT of the left eye showed severe intra and sub-retinal fluid with a central macular thickness of 477 OS, which is likely due to DME along with a dry form of ARMD having soft drusen. Patient 5 received one treatment of oscillating transpupillary therapy in the left eye. After the follow-up appointment, there was nearly complete resolution of edema in the left eye. The OCT showed a normal thickness of 187 microns (FIG. 13) and the VA improved as well to 20/100.

All references cited are incorporated by reference herein in their entirety. Other variations or embodiments will also be apparent to one of ordinary skill in the art from the above description and examples. Thus, the foregoing embodiments are not to be construed as construed as limiting the scope of the following claims.

What is claimed is:

1. A method for oscillatory thermotherapy of a biological tissue, the method comprising providing oscillatory electromagnetic energy to a site in an eye to effect thermotherapy by increasing a temperature in the tissue above body temperature and below a temperature at which protein denaturation is initiated in the tissue, the method producing a therapeutic effect at the target site, wherein the level of energy provided is determined by a pain sensation in the patient undergoing thermotherapy at the time the patient expresses a sensation of pain.

2. The method of claim 1 further comprising providing a biocompatible dye to the patient before, during, or after thermotherapy.

3. The method of claim 1 wherein therapy is selected from the group consisting of apoptosis, release of heat shock proteins, hyperthermic effect, and combinations thereof.

4. The method of claim 1 wherein thermotherapy increases fluid absorption in the tissue, increases circulatory flow to the tissue, and/or increases agent permeation in the tissue.

5. The method of claim 1 wherein the temperature of the tissue during treatment is between body temperature and below about 60° C.

6. The method of claim 1 wherein the temperature of the tissue during treatment is between body temperature and below about 55° C.

7. The method of claim 1 wherein the temperature of the tissue during treatment is between body temperature and below about 50° C.

8. The method of claim 1 further providing an agent selected from the group consisting of anti-inflammatory agents, steroids, non-steroidal anti-inflammatory drugs (NSAIDS), anti-vascular endothelial growth factor (VEGF) agents, anti-platelet derived growth factor (PDGF) agents, anti-proliferative agents, metalloproteinase inhibitors, immuno-modulating agents, protective agents, and combinations thereof.

9. The method of claim 1 for treating edema, abnormal vessels, neovascularization, leaking vessels, and/or scarring.

10. The method of claim 1 for treating age-related macular degeneration (ARMD), vascular damage, macular edema, optic nerve inflammation, pressure induced stress, glaucoma, contusion, trauma, oxidative stress, metabolic stress, and/or inflammation.

11. The method of claim 1 wherein tissue coagulation does not occur.

12. The method of claim 1 further comprising pre-heating the biological tissue prior to treatment with oscillatory energy.

13. The method of claim 12 wherein pre-heating comprises providing electromagnetic energy to the biological tissue at an energy level and for a duration that is substantially equivalent to the energy level and duration used in the oscillatory thermotherapy.

14. The method of claim 13 wherein the energy level and the duration are increased when the tissue being treated is greater than about 250 μm thick.

* * * * *